(12) United States Patent
Shapiro et al.

(10) Patent No.: US 8,129,173 B2
(45) Date of Patent: Mar. 6, 2012

(54) SELECTIVE ENZYMATIC ESTERIFICATION AND SOLVOLYSIS OF EPIMERIC VITAMIN D ANALOG AND SEPARATION OF THE EPIMERS

(75) Inventors: Evgeny Shapiro, Haifa (IL); Ayelet Fishman, Haifa (IL); Reinhard Effenberger, Haifa (IL); Asher Maymon, Petach Tikva (IL); Anchel Schwartz, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 1085 days.

(21) Appl. No.: 10/339,226

(22) Filed: Jan. 9, 2003

(65) Prior Publication Data
US 2003/0166226 A1 Sep. 4, 2003

Related U.S. Application Data

(60) Provisional application No. 60/348,082, filed on Jan. 10, 2002, provisional application No. 60/349,977, filed on Jan. 18, 2002.

(51) Int. Cl.
*C12P 7/02* (2006.01)
(52) U.S. Cl. .................................. 435/280; 514/167
(58) Field of Classification Search ................. 552/653; 435/280; 514/167
See application file for complete search history.

(56) References Cited

U.S. PATENT DOCUMENTS

| | | | |
|---|---|---|---|
| 4,594,340 A | 6/1986 | Partridge et al. | |
| 4,866,048 A | 9/1989 | Calverley et al. | |
| 4,963,492 A * | 10/1990 | Keller et al. | 435/280 |
| 4,996,158 A * | 2/1991 | Oda et al. | 435/280 |
| 5,401,731 A | 3/1995 | Calverley et al. | |
| 5,413,935 A * | 5/1995 | Patel et al. | 435/280 |
| 5,637,500 A | 6/1997 | Sih | |
| 5,665,716 A | 9/1997 | Kirsch et al. | |
| 5,786,348 A | 7/1998 | Bishop et al. | |
| 6,262,283 B1 | 7/2001 | Kinney et al. | |
| 6,531,459 B1 | 3/2003 | Steinmeyer et al. | |

FOREIGN PATENT DOCUMENTS

| | | |
|---|---|---|
| JP | 11-130711 | 5/1999 |
| JP | 2001-204484 A | 7/2001 |
| WO | WO 87/00834 | 2/1987 |
| WO | WO 92/12165 | 7/1992 |
| WO | WO 00/61777 | 10/2000 |
| WO | WO 01/02352 | 1/2001 |
| WO | WO 01/90396 | 11/2001 |
| WO | WO 03/106412 | 12/2003 |

OTHER PUBLICATIONS

Calverley, Martin J., "Synthesis of MC903, A Biologically Active Vitamin D Metabolite Analogue", 1987, Tetrahedron, vol. 43 No. 20, pp. 4609-4619.*
Calverley, Martin J., "A Biologically Active Vitamin D Metabolite Analogue," Tetrahedron, vol. 43, No. 20 (1987) pp. 4609-4619.
Calverley, Martin J., "The Seleno-Acetal Route to Side-Chain-Modified 1α-Hydroxy-Vitamin D Alalogues: Stereoselective Synthesis of the New 22Z Isomer of MC 903 (Calcipotriol)," Synlett, No. 3 (1990) pp. 157-159.
Supplementary Partial European Search Report, dated Nov. 6, 2007, from corresponding European patent application No. 03729607.6.
Calverley et al., "1α,24S-Dihydroxy-26,27-Cyclo-22-YNE-Vitamin $D_3$: The Side Chain Triple Bond Analogue of MC 903 (Calcipotriol)", *Bioorganic & Medicinal Chemistry Letters*, 3(9), 1841-1844 (1993).
Santaniello et al., "Lipase-Catalyzed Regio- and Stereoselective Acylation of Hydroxy Groups in Steroid Side Chains", *Monatshefte für Chemie*, 131:617-622 (2000).
Oshida et al., "Chemoenzymatic synthesis of 1α,24(R)-dihydroxycholesterol", *Tetrahedron: Asymmetry*, 10:2337-2342 (1999).
Fernandez et al., "Biocatalysis Applied to the Synthesis of Vitamin D Analogues", *Current Organic Chemistry*, 6:453-469 (2002).
Japanese Office Action, dated May 29, 2007, from corresponding Japanese Patent Application No. 2003-560181.
Barnett et al., AN 1941:4546 HCAPLUS, DN 35:4546, Sterol group. XLI. A new epimerization process. Journal of the Chemical Society, Abstracts (1940) 1390-3.

* cited by examiner

*Primary Examiner* — Karlheinz R Skowronek
*Assistant Examiner* — Ali Soroush
(74) *Attorney, Agent, or Firm* — Kenyon & Kenyon LLP

(57) ABSTRACT

Provided is a method of selectively enzymatically esterifying or selectively enzymatically solvolyzing epimers of analogs of vitamin D having a stereogenic center at C-24 that has a free or esterified OH group. The metod can be used, for example, for separating mixed epimers of the vitamin D analog.

24 Claims, No Drawings

SELECTIVE ENZYMATIC ESTERIFICATION AND SOLVOLYSIS OF EPIMERIC VITAMIN D ANALOG AND SEPARATION OF THE EPIMERS

RELATED APPLICATIONS

The present application claims the benefit of the filing date of U.S. Provisional Patent Applications No. 60/348,082, filed Jan. 10, 2002, and No. 60/349,977, filed Jan. 18, 2002.

FIELD OF THE INVENTION

The present invention relates to methods of selectively enzymatically esterifying and selectively enzymatically solvolyzing epimers at C-24 of analogs of vitamin D and esters thereof. The present invention further relates to methods of separating mixed epimers of analogs of vitamin D including a selective enzymatic esterification step or a selective enzymatic solvolysis step.

BACKGROUND OF THE INVENTION

Since the discovery of 1α, 25-dihydroxyvitamin $D_3$ (1,25-$(OH)_2D_3$), the hormonally active metabolite form of vitamin $D_3$, many analogs have been prepared in order to obtain active compounds with low calcemic affect. Much effort has been expended on modification of the vitamin D side chain. While the 1α hydroxyl group is essential for the hormonal activity, the C-25 hydroxyl group can be replaced with the C-24 hydroxyl group: see, for example, MC 903, (Structure I) or 1,24-$(OH)_2$ $D_3$ (Structure II).

In the preparation of Vitamin D analogs, a specific stereochemistry for the hydroxyl group at C-24 is necessary for full expression of the biological activity. Under current methodology, the required stereochemistry is introduced by one of three methods: (i) separation of diastereomeric mixture of C-24 hydroxyl epimers via chromatography (see, for example, Calverley, *Tetrahedron* 4609-4619, 1987); (ii) stereoselective reduction of the corresponding C-24 ketone, (see, for example, U.S. Pat. No. 6,262,283), or (iii) attachment of an enantiopure hydroxyl-carrying side-chain to the Vitamin D skeleton (see, for example, Calverley, *Synlett* 157-159, 1990).

The stereoselective synthesis is still an unfavorable process for scale up due to its multi-step nature and cost. The chromatographic separation of the epimeric mixture is most widely practiced. The difficulty in chromatographic separation stems from the fact that the two C-24 hydroxyl epimers do not differ greatly in their affinity for the adsorbent, and thus their retention times are too close to allow efficient separation in one chromatographic step. The present invention provides a means to greatly improve the efficacy of chromatographic separation.

SUMMARY OF THE INVENTION

In one aspect, the present invention relates to a method of selectively enzymatically esterifying the C-24 hydroxyl group of one epimer in a mixture of epimers of a vitamin D analog having a hydroxyl group at the stereogenic C-24 position thereof, especially wherein the mixed epimers are mixtures of C-24 epimers of compounds selected from compounds of general formula III or IX

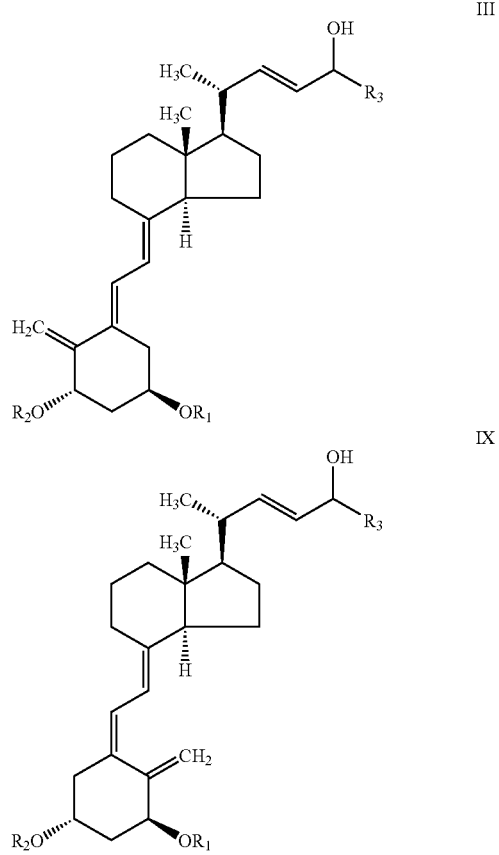

where $R_1$ and $R_2$ may be the same or different and represent hydrogen, or hydroxy protecting group, and $R_3$ is a lower alkyl, cycloalkyl, or aryl group, which method includes the steps of: providing a solution of mixed C-24 epimers of a vitamin D analog having a hydroxyl group at the C-24 position thereof and an esterifying agent, especially acetyl chloride, acetic anhydride, vinyl acetate, or vinyl butyrate, in an organic solvent, especially hexane or diisopropyl ether, and contacting the solution with a lipase, especially *Alcaligenes* sp. or *Pseudomonas* sp. lipase. The lipase can be but need not be fixed.

In another aspect, the present invention relates to a method of selectively enzymatically esterifying an epimeric mixture at C-24 of [1α, 3β,5E,7E,20R]-1,3-bis(tert-butyldimethylsiloxy)-20-(3'-cyclopropyl-3'(R,S)-hydroxy-1'-propenyl)-9,10-secopregna-5,7,10(19)-triene, especially wherein the C-24 OH epimer selectively esterified is [1α, 3β,5E,7E,20R]-1,3-bis(tertbutyldimethylsiloxy)-20-(3'-cyclopropyl-3'(R)-hydroxy-1'-propenyl)-9,10-secopregna-5,7,10(19)-triene, including the steps of providing a solution of the mixed C-24 epimers and an esterifying agent, for example acetyl chloride or vinyl acetate, in an organic solvent, for example hexane, and contacting the solution with a lipase, especially *Alcaligenes* sp. or *Pseudomonas* sp. lipase.

In another aspect, the present invention relates to a method of selectively enzymatically esterifying an epimeric mixture at C-24 of [1α, 3β,5Z,7E,20R]-1,3-bis(tert-butyldimethylsiloxy)-20-(3'-cyclopropyl-3'(R,S)-hydroxy-1'-propenyl)-9,10-secopregna-5,7,10(19)-triene, especially wherein the C-24 OH epimer selectively esterified is [1α, 3β,5E,7Z,20R]-1,3-bis(tertbutyldimethylsiloxy)-20-(3'-cyclopropyl-3'(R)-hydroxy-1'-propenyl)-9,10-secopregna-5,7,10(19)-triene, including the steps of providing a solution of the mixed C-24 epimers and an esterifying agent, for example acetyl chloride or vinyl acetate, in an organic solvent, for example hexane, and contacting the solution with a lipase, especially *Alcaligenes* sp. or *Pseudomonas* sp. lipase.

In another aspect, the present invention relates to a method of <<selectively enzymatically esterifying the C-24 hydroxyl group of one epimer in a mixture of epimers of a vitamin D analog having a hydroxyl group at the stereogenic C-24 position thereof, including the steps of: providing a solution of mixed C-24 epimers of a vitamin D analog having a hydroxyl group at the C-24 position thereof and an esterifying agent selected from acetyl chloride, acetic anhydride, vinyl acetate and vinyl butyrate in an organic solvent selected from hexane and diisopropyl ether, and contacting the solution with a lipase selected from *Alcaligenes* sp. lipase and *Psudomonas* sp lipase; wherein the mixed C-24 epimers are mixtures of C-24 epimers of compounds selected from compounds of general formula III or IX

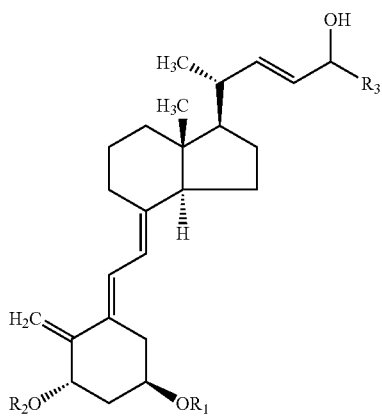

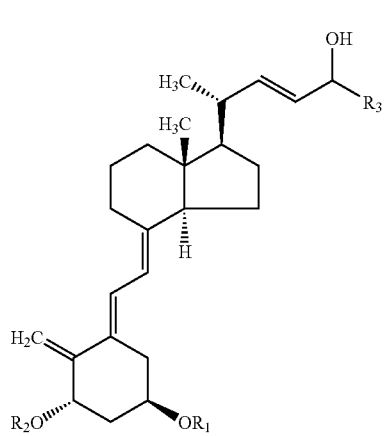

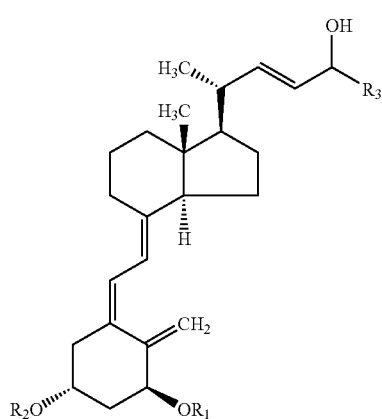

where $R_1$ and $R_2$ are hydrogen or tert-butyldimethylsiloxy and $R_3$ is a cyclopropyl or isopropyl group.

In a further aspect, the present invention relates to a method of enzymatically esterifying the C-24 hydroxyl group of a vitamin D analog having a hydroxyl group at the C-24 position thereof and selected from compounds of general formula III or IX

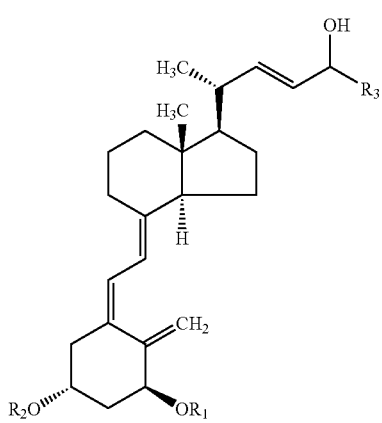

wherein $R_1$ and $R_2$ may be the same or different and represent hydrogen, or hydroxy protecting group, and $R_3$ is a lower alkyl, cycloalkyl, or aryl group comprising the steps of: providing a solution of the vitamin D analog having a hydroxyl group at the C-24 position thereof and an esterifying agent selected from the group consisting of the acyl halides, the acid anhydrides, and the vinyl esters of lower alkyl carboxylic acids having 2 to 6 carbon atoms in an organic solvent that is a linear or branched alkane having up to 12 carbons or a dialkyl ether, and contacting the solution with a lipase selected from *Alcaligenes* sp. lipase and *Psudomonas* sp lipase. The lipase can be free or fixed.

In another aspect, the present invention relates to a method of selectively enzymatically solvolyzing the esterified C-24 hydroxyl group of one epimer in a mixture of esterified C-24 epimers of a vitamin D analog having an esterified hydroxyl group at the C-24 stereogenic position thereof, especially wherein the mixed epimers are mixtures of esterified C-24 epimers of compounds selected from compounds of general formula III or IX

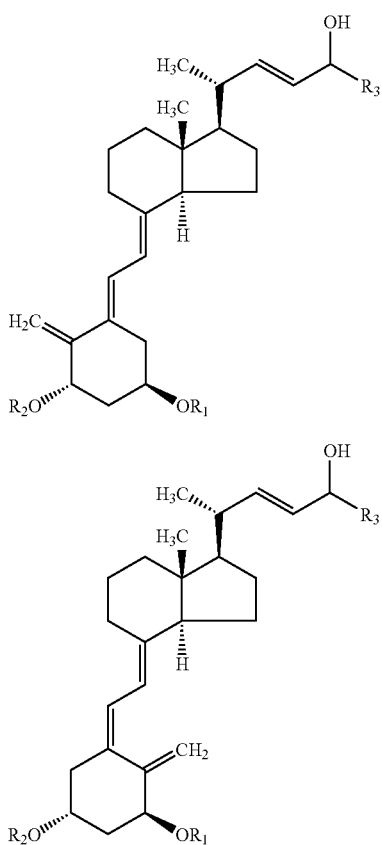

where $R_1$ and $R_2$ may be the same or different and represent hydrogen, or hydroxy protecting group, and $R_3$ is a lower alkyl, cycloalkyl, or aryl group, comprising the steps of: providing a solution of the mixed esterified C-24 epimers of a vitamin D analog having a hydroxyl group at C-24 and a solvolysis agent, especially water or a lower alkyl alcohol, in an organic solvent, especially hexane or diisopropyl ether, and contacting the solution with a lipase, especially *Alcaligenes* sp. lipase or *Pseudomonas* sp. lipase. The lipase can be but need not be fixed.

In yet another embodiment, the present invention relates to a method of selectively enzymatically solvolyzing, especially with water or a lower alkyl alcohol, the mixed C-24 epimers of an epimeric mixture of C-24 esters of [1α, 3β,5E,7E,20R]-1,3-bis(tert-butyldimethylsiloxy)-20-(3'-cyclopropyl-3'(R, S)-hydroxy-1'-propenyl)-9,10-secopregna-5,7,10(19)-triene, especially wherein the esterified C-24 OH epimer selectively solvolyzed is the ester of [1α, 3β,5E,7E,20R]-1, 3-bis(tertbutyldimethylsiloxy)-20-(3'-cyclopropyl-3'(R)-hydroxy-1'-propenyl)-9,10-secopregna-5,7,10(19)-triene.

In yet another embodiment, the present invention relates to a method of selectively enzymatically solvolyzing, especially with water or lower alkyl alcohol, the mixed C-24 epimers of an epimeric mixture of C-24 esters of [1α, 3β,5Z,7E,20R]-1, 3-bis(tert-butyldimethylsiloxy)-20-(3'-cyclopropyl-3'(R,S)-hydroxy-1'-propenyl)-9,10-secopregna-5,7,10(19)-triene, especially wherein the esterified C-24 OH epimer selectively solvolyzed is the ester of [1α, 3β,5Z,7E,20R]-1,3-bis(tertbutyldimethylsiloxy)-20-(3'-cyclopropyl-3'(R)-hydroxy-1'-propenyl)-9,10-secopregna-5,7,10(19)-triene.

In yet a further aspect, the present invention relates to a method for making a diasteriomerically pure vitamin D analog including the step of enzymatically selectively esterifying at the 24 position a vitamin D analog having a hydroxyl group at the 24 position.

In another aspect, the present invention relates to a method for making a diasteromerically pure vitamin D analog including the step of selectively enzymatically solvolyzing the C-24 ester of one epimer in a mixture of epimers of a vitamin D analog having an esterified hydroxyl group at the C-24 stereogenic center thereof.

In still a further aspect, the present invention relates to a preocess for making calcipotriene, (5Z, 7E, 22E, 24S)-24-cyclopropyl-9,10-secochola-5,7,10(19), 22-tetraene-1α-3β-24-triol, by chromatographically separating mixed epimers of a vitamin D analog having an OH group at a C-24 stereogenic center by a method including a step selected from selective enzymatic esterification and selective enzymatic solvolysis wherein; when selective enzymatic solvolysis is chosen, the OH group at C-24 of both epimers is first esterified, and when selective esterification is chosen, vinyl acetate is the esterification agent, and wherein the selective esterification or selective solvolysis is effected with fixed or free *Alcaligenes* sp. lipase or *Pseudomanas* sp. lipase.

In yet a further aspect, the present invention relates to A method of separating mixed epimers of a vitamin D analog having a hydroxyl group in the 24 position, wherein C-24 is the epimeric center, especially wherein the mixed C-24 epimers are mixtures of C-24 epimers of compounds selected from compounds of general formula III or IX where $R_1$ and $R_2$ may be the same or different and represent hydrogen, or hydroxy protecting group, and $R_3$ is a lower alkyl, cycloalkyl, or aryl group, including the steps of: selectively enzymatically esterifying the hydroxyl group at C-24 of one epimer, as discussed above, and chromatographically separating esterified epimers from nonesterified epimers. This method is especially suited when the C-24 epimers are an epimeric mixture at C-24 of [1α, 3β,5E,7E,20R]-1,3-bis(tert-butyldimethylsiloxy)-20-(3'-cyclopropyl-3'(R,S)-hydroxy-1'-propenyl)-9,10-secopregna-5,7,10(19)-triene or an epimeric mixture at C-24 of [1α, 3β,5Z,7E,20R]-1,3-bis(tert-butyldimethylsiloxy)-20-(3'-cyclopropyl-3'(R,S)-hydroxy-1'-propenyl)-9,10-secopregna-5,7,10(19)-triene.

In yet a further aspect, the present invention relates to a method of separating mixed C-24 epimers of a vitamin D analog having a hydroxyl group in the C-24 position, wherein C-24 is the epimeric center, including the steps of: esterifying the C-24 hydroxyl group of both epimers, selectively enzymatically solvolyzing the C-24 ester so formed of one of the epimers, and chromatographically separating selectively solvolyzed epimer from nonsolvolyzed epimer. This method is particularly applicable when the mixed C-24 epimers are mixtures of C-24 epimers of compounds selected from compounds of general formula III or IX

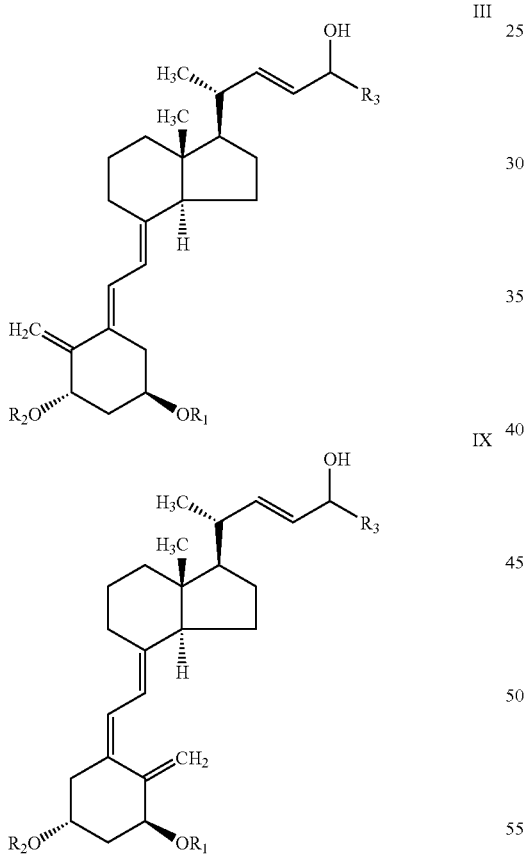

where $R_1$ and $R_2$ may be the same or different and represent hydrogen, or hydroxy protecting group, and $R_3$ is a lower alkyl, -cycloalkyl, or aryl group.

DETAILED DESCRIPTION OF THE INVENTION

As used herein, a vitamin D analog means any compound having the basic cholecalciferol or ergocalciferol structure and modifications thereof, including those in which an exocyclic double bond of the A ring is at different positions and/or in which the structure of the side-chain attached to the D ring at carbon 17 is varied, particularly those modifications (analogs) in which the side chain has a cyclopropyl or isopropyl group at C-24.

Because vitamin D is a steroid, we retain, to the extent possible, the ring designation and numbering system from the parent compound, cholesterol. Representative vitamin D derivatives that are objects of present invention are illustrated below (structures I and II).

Structures I and II

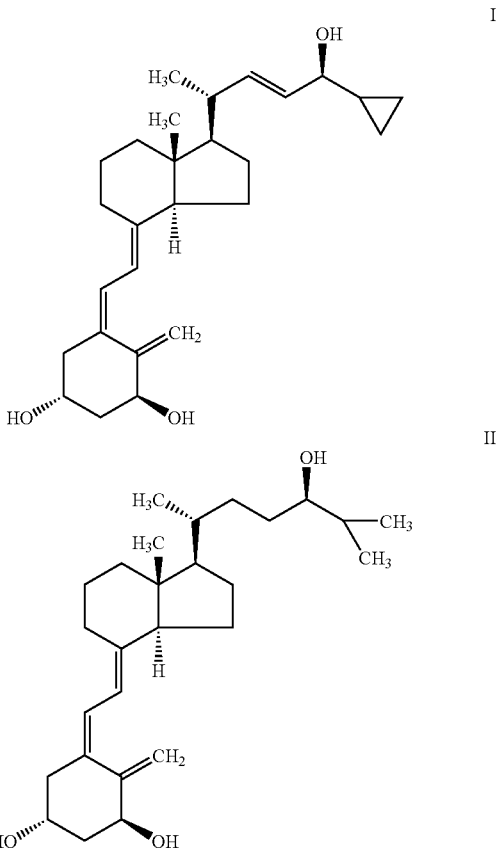

Epimers are known as diastereomers that have opposite configuration (R or S) at only one of multiple tetrahedral stereogenic centers in molecules, like the vitamin D analogs to which the present invention is directed, having multiple stereogenic centers. Epimers of vitamin D analogs useful in the practice of the present invention are diastereomers with respect to the configuration at C-24.

Designation of, for example, C-24 as the epimeric center of a pair of enantiomers therefore implies that the configuration at the other stereogenic centers of the pair are the same.

Unless otherwise required by the context, as used herein in connection with epimers and mixtures of epimers of vitamin D analogs having a hydroxyl group at the C-24 position, selective enzymatic esterification and selectively enzymatically esterified mean that the hydroxyl group at the 24 position of one epimer is esterified with an esterification agent with the aid of an enzyme to the substantial exclusion of esterification of the hydroxyl group at the 24 position of the other epimer. Substantial exclusion implies that, of all molecules esterified, at least about 80 mole-% of one epimer and not more than about 20% of the other epimer is esterified (diastereomer ratio 80:20). Preferably the diastereomer ratio is at least 90:10; most preferably it is at least 95:5. The skilled artisan will know to optimize the process variables hereinbelow discussed to achieve the desired diasteromer ratio.

Unless otherwise required by the context, as used herein in connection with epimers and mixtures of epimers of vitamin D analogs having an ester group (e.g. acetate) at the 24 position, selective enzymatic solvolysis and selectively enzymatically solvolyzed mean that the ester group at the 24 position of one epimer is solvolyzed to the substantial exclusion of solvolysis of the ester group at the 24 position of the other epimer. Substantial exclusion implies that, of all molecules solvolyzed, at least about 80 mole-% of one epimer and not more than about 20% of the other epimer are solvolyzed (diastereomer ratio 80:20). Preferably the ratio is at least 90:10; most preferably it is at least 95:5. The skilled artisan will know to optimize the process variables hereinbelow discussed to achieve the desired diasteromer ratio.

As used herein, lower alky means a linear or branched alkyl group, which may be cyclic or acyclic, having one to ten carbon atoms. The isopropyl group and the cyclopropyl group are examples of lower alkyl groups.

As used herein, aryl is a substituted or unsubstituted aromatic group having six to twelve carbon atoms. The phenyl group is an example of an aryl group.

In the present invention, solvolysis is carried out with a solvolysis agent, preferably a polar protic solvent. Preferred polar protic solvents are water and lower aliphatic alcohols.

Enzymatic and enzymatically mean that the respective process is effected with an enzyme. Preferred enzymes are lipases. *Alcalagenes* sp. lipase and *Pseudomonas* sp. lipase are preferred lipases for use in the practice of the present invention. The enzyme can be fixed (immobilized) or free. Procedures for immobilizing enzymes are well known in the art.

As used herein, esterification of a hydroxyl group is synonymous with acylation and means any of the reactions known in the art that replace the hydrogen of an alcoholic hydroxyl group with an acyl group (e.g. RC(O)—).

The separation methods of the present invention employ either a selective enzymatic esterification step or a selective enzymatic solvolysis step and, in preferred embodiments, a chromatographic step. The selective enzymatic esterification step is preferred when compounds having an isopropyl group (II) or a cyclopropyl group (I) at C-24 are the object of the process.

We have now found that a mixture of C-24 epimers of vitamin D analogs having a hydroxyl group at an epimeric center at C-24 can be selectively esterified at the 24 position in the presence of an enzyme, preferably a lipase, producing a mixture of the C-24 ester of one epimer and the original C-24 alcohol of the non-esterified epimer. This is illustrated below in scheme I. It is not important to the present invention which epimer is selectively esterified.

We have also found that an epimeric mixture of C-24 esters of vitamin D analogs can be selectively solvolyzed, in the presence of an enzyme, preferably a lipase, to yield a mixture of the C-24 ester of one epimer and the C-24 alcohol epimer of the other. This is illustrated below in scheme II. Scheme II is illustrated with acetyl chloride, but other esterification agents are equally useful. It is not important to the practice of the present invention which epimer is selectively solvolyzed. We discovered that an ester can be formed at the C-24 position of vitamin D analogs, without simultaneous esterification of hydroxyl groups on the A ring of the vitamin D analog. Thus, the present method can be practiced without having to protect OH groups on, for example, the A ring of the vitamin D derivative.

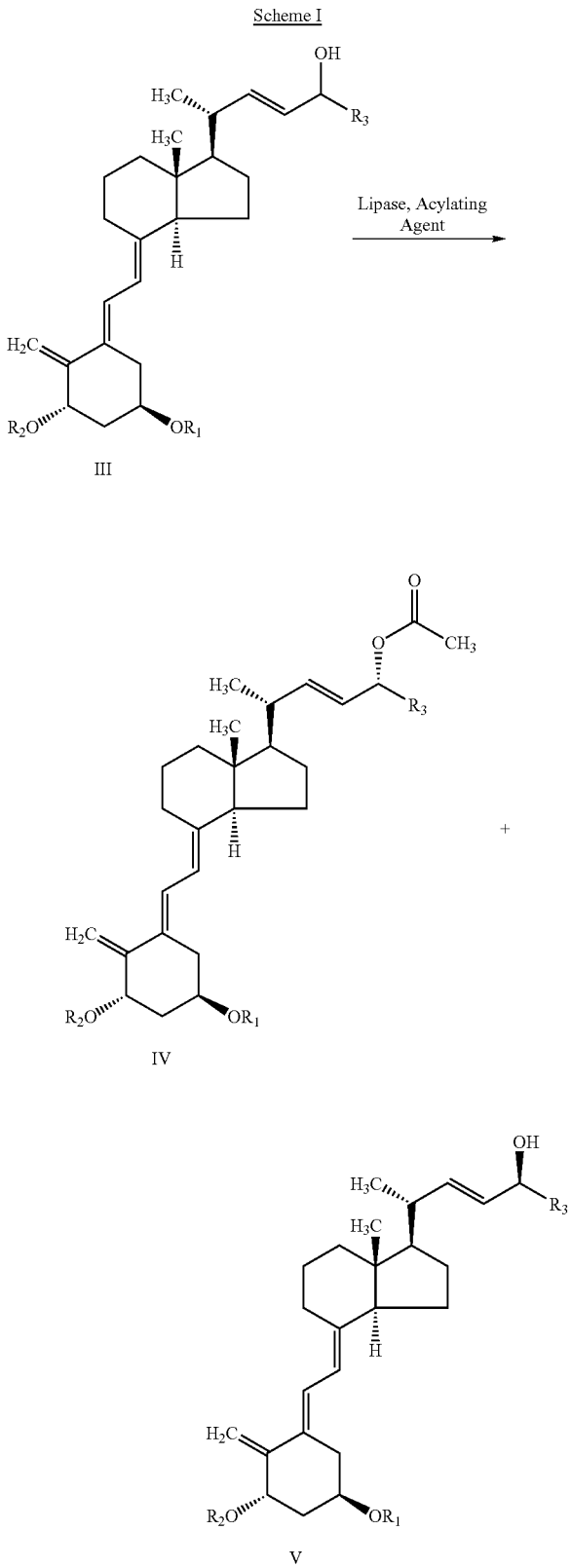

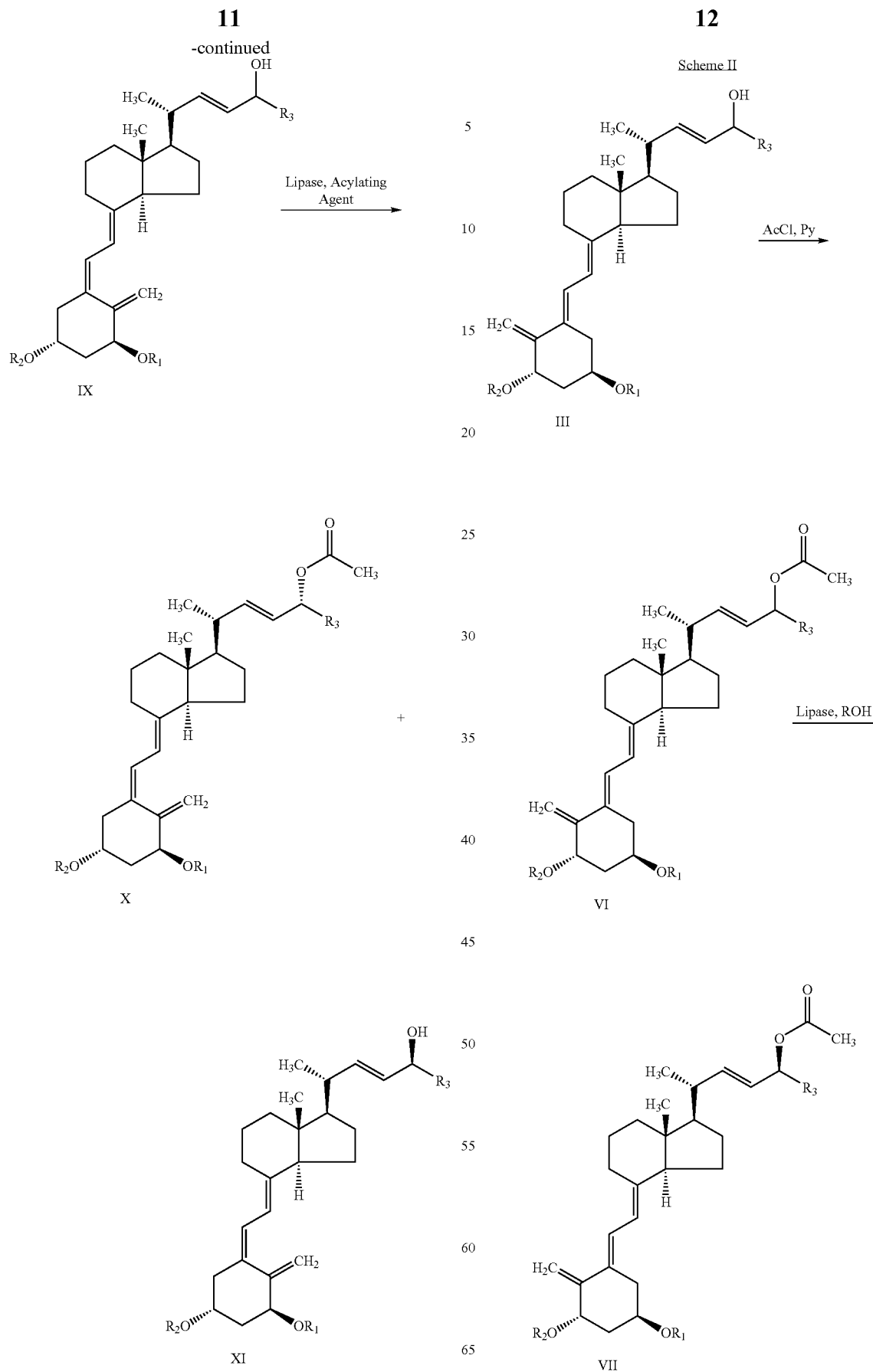

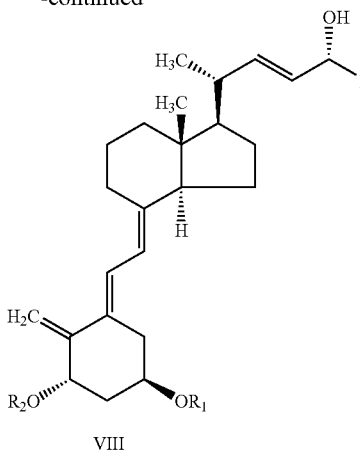

VIII

Although it is not necessary in the practice of the invention, it may be convenient to protect the hydroxyl groups on the A-ring of the vitamin D analogs. Any of the methods for protecting the hydroxyl groups as are known in the art can be used, if desired. The tert-butyldimethylsilyl group is but one example of hydroxyl protecting group that can be used in the practice of the present invention.

In one embodiment, the present invention provides for selective enzymatic esterification of a vitamin D analog. In selective enzymatic esterification, the vitamin D analogue (e.g., general structure—III or IX), consisting of a mixture of C-24 OH epimers, and an esterification (acylating) agent (A), are dissolved in an organic solvent (S1) to provide a solution that is then contacted with an enzyme (E), preferably a lipase. Suitable solvents (S1) include linear and branched alkanes having up to about 12 carbon, for example hexane, and dialkyl ethers, for example diisopropyl ether. Alkyl and alkeny esters are examples of suitable esterification agents. Vinyl acetate is a preferred esterification agent. The solution is contacted (e.g. stirred) with enzyme (E) at a specified temperature (T) for a period of time (t). Any temperature that does not destroy the activity of the enzyme can be used. Temperatures between about 20° C. and about 40° C. are preferred. The skilled artisan will know to adjust the reaction time according to the progress of the reaction. The progress of the esterification reaction can be followed by high pressure liquid chromatography (HPLC). A Merck-Hitachi Model 6200 A using 0.5% amyl alcohol in hexane as the mobile phase is suitable for use. The skilled artisan will also know to adapt a suitable analytical method from the preparative chromatographic method described below. The same analytical method can be used in all embodiments of the present invention. The esterification is stopped when enough of the undesired epimer has been esterified to ensure a diastereomeric excess of the C-24 alcohol of at least about 80%, preferably at least about 95%.

At this point, the enzyme is separated (removed) by suitable means as will be known to the skilled artisan, for example filtration or centrifugation to mention just two, and the filtrate is concentrated.

In another embodiment, the present method provides for selective enzymatic solvolysis of an esterified vitamin D analog. Selective enzymatic solvolysis can be illustrated with selective enzymatic alcoholysis, in which case the step can also be called selective enzymatic transesterification. The vitamin D analogue (e.g., general structure—III), consisting of a mixture of C-24 OH epimers, is esterified to a mixture of C-24 epimeric esters via standard methods well known to the skilled artisan, such as using an acyl halide, acid anhydride, or an active ester such as a vinyl alkanoate. This mixture of epimeric esters is then dissolved in an organic solvent (S1), especially a lower alkane or dialkyl ether as above, containing a solvolysis agent, especially a lower alkyl alcohol (R—OH) or water, to provide a solution that is contacted with an enzyme (E), preferably a lipase. The contacting (e.g. mixing) is at a specified temperature (T) for a period of time (t) and the progress of the solvolysis reaction is followed by HPLC. The solvents, solvolysis agents, temperatures, and times useful for selective enzymatic esterification are also useful in the present embodiment. The reaction is stopped when enough of the C-24 alcohol epimer has been selectively formed in the required diastereomeric excess of at least about 80%, preferably above 95%. In this embodiment, it is preferred that the C-24 OH epimer formed by transesterification not be the desired (sought) epimer.

At this point, the enzyme is removed by filtration (or other suitable means such as centrifugation) and the filtrate is concentrated.

In yet another embodiment, selective enzymatic solvolysis is carried out with water. In this case the step can be referred to as selective enzymatic hydrolysis. The vitamin D analogue (e.g., general structure—III), consisting of a mixture of C-24 OH epimers, is esterified to a mixture of C-24 epimeric esters via standard methods (such as using an acyl halide, acid anhydride or an active ester such as a vinyl alkanoate etc). This mixture of epimeric esters is then dissolved in an organic solvent (SI) containing water and an enzyme (E) such as a lipase. The mixture is stirred at a specified temperature (T) for a period of time (t) and the progress of the hydrolysis reaction is followed by HPLC. The reaction is stopped when enough of the C-24 alcohol epimer has been selectively formed in the desired diastereomeric excess of at least about 80%, preferably at least about 95%. In this embodiment, it is preferred that the C-24 alcohol formed is the C-24 alcohol of the undesired epimer and the nonhydrolyzed ester is the ester of the desired C-24 OH epimer.

At this point, the enzyme is removed by appropriate means as will be apparent to the skilled artisan, for example filtration or centrifugation to mention just two. The filtrate is concentrated.

Because of the now much larger difference in polarity between the C-24 alcohol and the C-24 ester, the selectively esterified or selectively solvolyzed epimers now have well-resolved elution times, thereby allowing the complete separation of the mixtures, however prepared, in a single-pass by, for example, column chromatography as described below. Accordingly, in another embodiment, the present invention provides a method of separating C-24 epimers of vitamin D analogs having a hydroxyl group at the C-24 stereogenic center that includes a step selected from selective enzymatic esterification and selective enzymatic solvolysis To obtain separate epimers, the concentrate from selective enzymatic esterification or selective enzymatic solvolysis is then loaded onto a chromatographic column, described below, and eluted by a suitable solvent or solvent mixture (S2) so as to separate the C-24 alcohol (V) from the C-24 ester (IV) and, similarly, to separate XI from X, as described in Scheme I. In Scheme I, the ester formed at C-24 is an acetate, but other esters, for example the butyrate, are equally useful. In another embodiment the C-24 alcohol is separated from the C-24 ester, preferably the ester of of the desired epimer (Scheme II). In Scheme II, the esterifying agent is an acyl chloride, but other esterification agents, for example acid anhydrides, are equally useful.

Separated ester can be converted to the desired alcohol by methods well known in the art, whereby one obtains esentially stereochemically pure C-24 hydroxy epimers from a mixture of epimers. Thus, is does not matter which of the epimers is desired, because the methods described herein can produce either of them.

Examples of values that can be selected for several reaction parameters in the practice of the several embodiments of the present invention are collected below.

| Parameter | Suitable type or condition | Comment |
|---|---|---|
| Substrate | Compound III mixture 65:35 (mixture of compounds VIII and V) | Any amount of compound VIII in the mixture |
| Substrate concentration | 25-50% (w/v) | 1-80% |
| Other substrates | Compound of structure IX | |
| Enzyme | Lipase from Pseudomonas sp. or Alcaligenes sp. | Lipases from microbial, mammalian or plant origin |
| Enzyme form | Crude or immobilized | |
| Acylating agent | Vinyl acetate/vinyl butyrate/vinyl propionate | Ethyl acetate, butyl acetate, ethylphenyl acetate, 222-trifluoroethyl butyrate |
| Acylating agent amount | Vinyl acetateA/III 2-3 mol ratio | Can be used a solvent |
| Solvent | hexane | Hexane, diisopropyl ether, toluene, dichloromethane, tetrachloromethane, acetone, methyl isobutyl ketone |
| Solvent mixture for chromatography | 3%- ethyl acetate in hexane | 3-10% ethyl acetate in hexane |
| Reaction time | 2-3 hours | 1-24 hours |
| Reaction temperature | 25-35° C. | 10-60° C. |

Scheme III

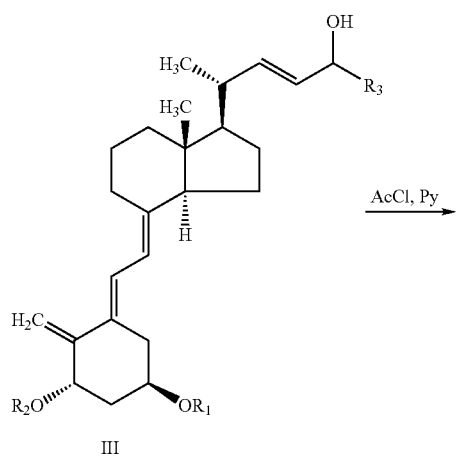

III

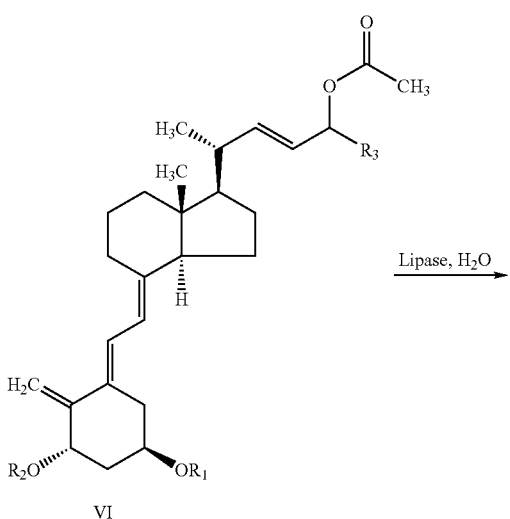

VI

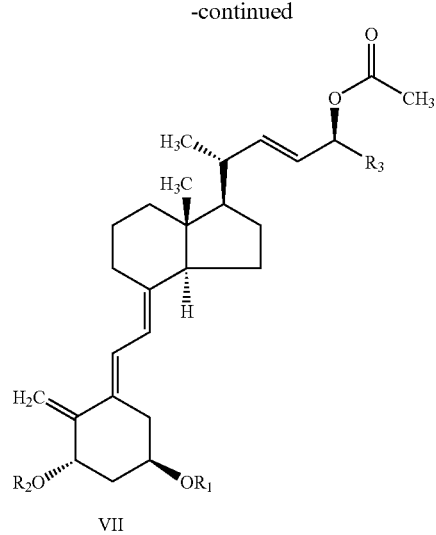

VII

+

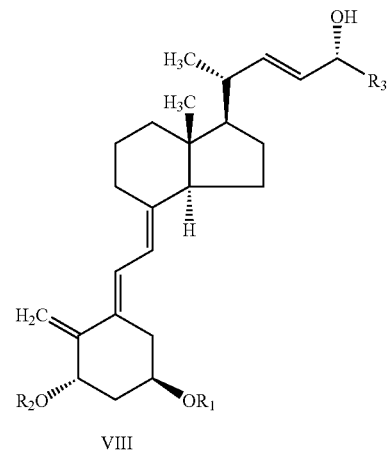

VIII

For the chromatography step, any combination of stationary phase (packing) and eluent that is capable of resolving the mixture of C-24 alcohol and C-24 ester can be used. Such combinations can be readily determined by the skilled artisan by routine experimentation. An example of a preferred stationary phase is treated silica.

Column chromatography, useful for the separation of selectively esterified or selectively solvolyzed vitamin D analogs of the present invention is well known to those in the art of pharmaceutical chemistry. The technique employs a column packed with a stationary phase, for example treated silica, onto which a sample to be separated is loaded. The sample is then eluted with a suitable eluent. Elution can be isocratic or so-called solvent programmed, wherein the composition of the eluent is varied regularly (e.g. linearly) or irregularly (e.g. stepwise) over time. Pre-treated silica gel, well known in the chromatographic arts, is a suitable stationary phase. Elution with 5% (v/v) ethyl acetate in hexane followed by neat ethyl acetate is but one example of an elution program that produces the desired separation. Others suitable eluents will be deduced by the skilled artisan through routine methods development.

3. EXAMPLES

The present invention will be even more fully understood by way of the following nonlimiting examples.

Example 1

Selective Enzymatic Esterification

To a stirred solution of C-24 epimeric alcohol mixture of structure III, $R_1=R_2$=tert butyldimethylsilyl and $R_3$=cyclopropyl, (20 gr, 31.2 mmol) and vinyl acetate (5.8 ml, 62.4 mmol) in hexane (60 ml) was added 0.56 gr Alcaligenes sp. Lipase. The mixture was stirred for 3 hours at 25+3° C. after which time the HPLC analysis showed essentially complete conversion of epimer C-24 (R) to the acetate. The remaining nonesterified C-24 (S) alcohol was >99% diastereomeric excess (by HPLC). The solution was filtered and concentrated to dryness. The residue was chromatographed on pre-treated silica gel with 5% ethyl acetate in hexane then with ethyl acetate to give C-24 acetate compound IV (11 gr) and C-24 alcohol compound V (7.4 gr).

The purity profile of the product was as follows.

|          | Purity profile | | | Instrument and method |
|----------|------|------|------|-----------------------|
| Compound | IV   | V    | VIII | Merck-Hitachi         |
| IV       | 93.1 | 0.2  | —    | Model: L-6200A intelligent pump. Mobile phase : 0.5% amyl alcohol in hexane |
| V        | 0.5  | 89.0 | 1.6  |                       |

Example 2

Selective Enzymatic Esterification 0.5 g of *Alcaligenes* sp. lipase was immobilized onto 4 g Eupergit C (Rohm, Germany) according to a known procedure recommended by the supplier. To a round bottom flask containing 0.3 g (0.47 mmol) C-24 epimeric alcohol mixture III, $R_1=R_2$=tert-butyldimethylsilyl and $R_3$=cyclopropyl, (65:35 isomer ratio), 0.43 ml (4.7 mmol) vinyl acetate and 3.57 ml hexane, 400 mg of immobilized enzyme was added. The mixture was stirred at 35° C. for 4 hours, after which time the HPLC analysis showed the presence of 30% compound IV, 35% compound VIII and 35% unreacted compound of structure V.

Example 3

Selective Enzymatic Esterification

To a vial containing 100 mg (0.16 mmol) of mixed C-24 epimers of C-24 alcohol of structure III, with $R_1=R_2$=tert-butyldimethylsilyl and $R_3$=cyclopropyl, (65:35 isomer ratio), 0.044 ml (0.47 mmol) vinyl acetate and 1.5 ml diisopropyl ether, 10 mg of *Alcaligenes* sp. lipase was added. The mixture was stirred at room temperature for 2 hours after which time the HPLC analysis showed the presence of 65% compound IV and 35% compound of structure V.

Example 4

Selective Enzymatic Esterification

To a vial containing 100 mg (0.16 mmol) of mixed C-24 epimers of C-24 alcohol III, $R_1=R_2$=tert-butyldimethylsilyl and $R_3$=cyclopropyl, (65:35 isomer ratio), 0.044 ml (0.47 mmol) vinyl acetate and 1.5 ml carbon tetrachloride, 10 mg of Alcaligenes sp. lipase was added. The mixture was stirred at room temperature for 2 hours after which time the HPLC analysis showed the presence of 65% compound IV and 35% compound V

Example 5

Selective Enzymatic Esterification

To a vial containing 100 mg (0.16 mmol) of mixed C-24 epimers of C-24 alcohol of structure III, $R_1=R_2$=tert-butyldimethylsilyl and $R_3$=cyclopropyl, (65:35 isomer ratio), 0.140 ml (1.6 mmol) vinyl acetate and 0.36 ml hexane, 50 mg of *Pseudomonas* sp. lipase was added. The mixture was stirred at room temperature for 1 hour after which time the HPLC analysis showed the presence of 65% compound of structure IV and 35% compound of structure V.

Example 6

Selective Enzymatic Esterification

To a round bottom flask containing 5 g (7.8 mmol) of mixed C-24 epimers of C-24 alcohol of structure III, $R_1=R_2$=tert-butyldimethylsilyl and $R_3$=cyclopropyl, (65:35 isomer ratio), 1.26 ml (15.6 mmol) vinyl butyrate and 8.7 ml hexane, 250 mg of *Alcaligenes* sp. lipase was added. The mixture was stirred at room temperature for 2 hours after which time the HPLC analysis showed the presence of 65% C-24 butanoate (e.g. butanoate analog of structure IV) and 35% compound V. The alcohol was separated from the butyl ester by chromatography on pre-treated silica gel.

Example 7

Selective Enzymatic Esterification

To a round bottom flask containing 300 mg (0.468 mmol) a mixture of C-24 epimers of C-24 alcohol of structure III, $R_1=R_2$=tert-butyldimethylsilyl and $R_3$=cyclopropyl, (65:35 isomer ratio) and, 4 ml ethyl acetate, 50 mg of *Alcaligenes* sp. lipase was added. The mixture was stirred at 35° C. for 24 hours after which time the HPLC analysis showed the presence of 45% compound of structure IV, 20% compound of structure VIII and 35% compound of structure V.

Example 8

Selective Enzymatic Esterification

To a round bottom flask containing 10 g (15.6 mmol) compound VIII, $R_1=R_2=$tert-butyldimethylsilyl and $R_3=$cyclopropyl, 2.9 ml (31.3 mmol) vinyl acetate and 17.1 ml hexane, 800 mg of *Alcaligenes* sp. lipase was added. The mixture was stirred at room temperature for 4 hours after which time the HPLC analysis showed the presence of 99% compound IV.

Example 9

Selective Enzymatic Esterification

To a vial containing 1 g (1.56 mmol) of C-24 epimeric alcohol mixture IX, $R_1=R_2=$tert-butyldimethylsilyl and $R_3=$cyclopropyl, (65:35 isomer ratio), 0.44 ml (4.68 mmol) vinyl acetate, 2.9 ml hexane and 250 mg of *Alcaligenes* sp. lipase was added. The mixture was stirred at room temperature for 3 hours after which time the HPLC analysis showed the presence of 65% compound X and 35% compound XI.

Example 10

Selective Enzymatic Esterification

To a vial containing 25 mg (0.06 mmol) C-24 epimeric alcohol mixture IX, where $R_1=R_2=$H, and $R_3$ is cyclopropyl, (50:50 isomer ratio), 0.044 ml (0.48 mmol) vinyl acetate, 0.5 ml acetone, 2 ml diisopropyl ether and 50 mg of *Alcaligenes* sp. lipase was added. The mixture was stirred at room temperature for 3 hours after which time the HPLC analysis showed the presence of 50% compound X and 50% compound XI. The acetylation took place on the C-24 hydroxy position only, was confirmed by H-NMR.

Example 11

Selective Solvolysis

To a round bottom flask containing 2 g (3.2 mmol) C-24 epimeric alcohol mixture III, $R_1=R_2=$tert-butyldimethylsilyl and $R_3=$cyclopropyl, (65:35 isomer ratio) dissolved in 8 ml pyridine, acetic anhydride (0.4 ml, 4.2 mmol) was added dropwise while maintaining a temperature of 5° C. The temperature was raised to 45° C. and the reaction left for 24 hours. The mixture was extracted with 10 ml hexane and the organic phase was evaporated. 1.7 g of mixture VI acetates was obtained. To a vial containing 100 mg (0.15 mmol) mixture VI (65:35 isomer ratio), 0.041 ml (0.45 mmol) ethanol and 2 ml hexane, 200 mg of *Alcaligenes* sp. lipase was added. The mixture was stirred at room temperature for 72 hours after which time the HPLC analysis showed the presence of 65% compound VIII and 35% compound VII.

Example 12

Selective Solvolysis

To a vial containing 100 mg (0.15 mmol) C-24 epimeric acetate mixture VI, $R_1=R_2=$tert-butyldimethylsilyl and $R_3=$cyclopropyl, (65:35 isomer ratio), 5 ml $H_2O$, 1.5 ml hexane and 250 mg of *Alcaligenes* sp. lipase was added. The mixture was stirred at room temperature for 260 hours after which time the HPLC analysis showed the presence of 32% compound VII and 62% compound VIII.

Example 13

Preparation Calcipotriene (MC 903)

A solution of alcohol of structure V with $R_1=R_2=$tert-butyldimethylsilyl and $R_3=$cycloprpyl (15.3 g, 24 mmol), 9-acetylanthracene (1.6 g, 7.2 mmol), and triethylamine in toluene (350 µL in 1200 ml) contained in a photochemical reactor and cooled to 5-8° C. was irradiated with light from a high pressure ultra-violet lamp to completion (~45 min.). The reaction mixture was transferred to an evaporator. The reactor was rinsed with 2×100 ml toluene and the rinsings were added to the evaporator. The mixture was evaporated to dryness under vacuum to yield crude alcohol of structure XI 15.3 g.

The alcohol XI was dissolved in THF (450 ml) and tetrabutylammonium fluoride (45 ml, 45 mmol) was added to the solution. The resulting mixture was heated at 40° C. for 2 hours under an atmosphere of nitrogen and evaporated to dryness. The residue was dissolved in ethyl acetate (1200 ml) and the solution was washed with 2% sodiumbicarbonate solution (2×150 ml) followed with brine (1×250 ml). The solution was dried over $Na_2SO_4$ and evaporated to dryness. The residue was chromatographed on silica gel (1200 g) eluted with mixture of ethyl acetate in hexane. Collection the appropriate fractions (checked by TLC) and evaporation gave 7 g of a foamy material.

3 g of the product were crystallized from acetone then from methyl formate to give 1.3 g calcipotriene.

What is claimed is:

1. A method of selectively enzymatically esterifying the C-24 hydroxyl group of one epimer in a mixture of C-24 epimers of a compound of general formula III or IX:

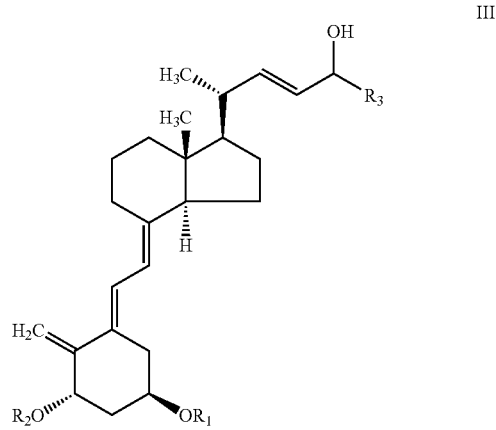

-continued

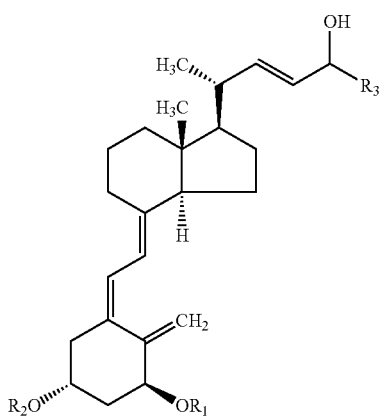

IX where R₁ and R₂ may be the same or different and independently represent hydrogen, or hydroxy protecting group, and R₃ is cyclopropyl or isopropyl, comprising the steps of:
   a) providing a solution of said mixture of C-24 epimers and an esterifying agent in an organic solvent, wherein the esterifying agent is selected from the group consisting of alkyl and vinyl esters; and
   b) contacting the solution with a lipase, wherein the lipase is *Alcaligenes* sp. lipase or *Psudomonas* sp lipase; wherein at least one of R₁ and R₂ is —H; and
wherein the epimer that is selectively enzymatically esterified is one having an R absolute configuration.

2. The method of claim 1 wherein R₁ and R₂ are both H.

3. The method of claim 1 wherein the lipase is *Alcaligenes* sp lipase.

4. The method of claim 2 wherein the lipase is *Pseudomonas* sp. lipase.

5. The method of any one of claims 1-4 wherein the lipase is fixed.

6. The method of any one of claims 1-4 wherein the lipase is free.

7. The method of claim 1 or claim 3 wherein the mixed C-24 epimers are an epimeric mixture at C-24 of [1α,3β,5E,7E,20R]-1,3-bis(tert-butyldimethylsiloxy)-20-(3'-cyclo-propyl -3'(R,S)-hydroxy-1'-propenyl)-9,10-secopregna-5,7,10(19)-triene.

8. The method of claim 7 wherein the C-24 OH epimer selectively esterified is [1α,3β,5E,7E,20R]-1,3-bis(tertbutyldimethylsiloxy)-20-(3'-cyclopropyl-3'(R)-hydroxy-1'-propenyl)-9,10-secopregna-5,7,10(19)-triene.

9. The method of claim 1 or claim 3 wherein the mixed epimers are an epimeric mixture at C-24 of [1α,3β,5Z,7E,20R]-1,3-bis(tert-butyldimethylsiloxy)-20-(3'-cyclo-propyl -3'(R,S)-hydroxy-1'-propenyl)-9,10-secopregna-5,7,10(19)-triene.

10. The method of claim 9 wherein the C-24 OH epimer selectively esterified is [1α,3β,5Z,7E,20R]-1,3-bis(tertbutyldimethylsiloxy)-20-(3'-cyclopropyl-3'(R)-hydroxy-1'-propenyl)-9,10-secopregna-5,7,10(1-9)-triene.

11. The method of any one of claims 1-4 wherein the esterifying agent is selected from the group consisting of alkyl and vinyl esters of lower alkyl carboxylic acids having 2 to 6 carbon atoms.

12. The method of claim 11 wherein the esterifying agent is selected from the group consisting of ethyl acetate, vinyl acetate, and vinyl butyrate.

13. The method of any one of claims 1-4 wherein the organic solvent is a linear or branched alkane having up to 12 carbon atoms, a dialkyl ether, or an alkyl ester of an alkyl carboxylic acid.

14. The method of claim 12 wherein the solvent is selected from the group consisting of hexane, ethyl acetate, carbon tetrachloride and diisopropyl ether.

15. The method of claim 13 wherein the solvent is selected from the group consisting of hexane, ethyl acetate, carbon tetrachloride and diisopropyl ether.

16. A method of selectively enzymatically esterifying the C-24 hydroxyl group of one epimer in a mixture of C-24 epimers of a compound of general formula III or IX

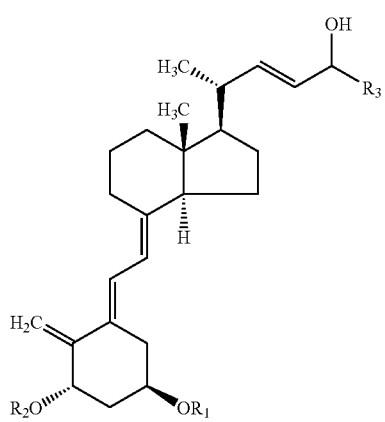

III

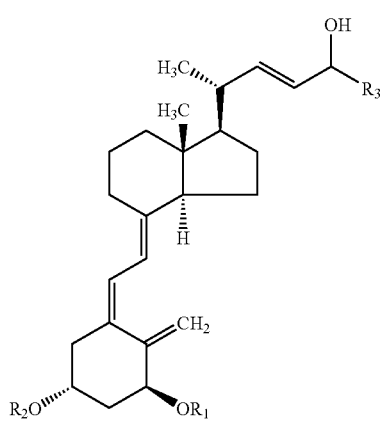

IX where R₁ and R₂ independently represent hydrogen, or hydroxy protecting group, and R₃ is cyclopropyl or isopropyl, comprising the steps of:
   a) providing a solution of said mixture of C-24 epimers and an esterifying agent in an organic solvent, wherein the esterifying agent is selected from the group consisting of alkyl and vinyl esters; and
   b) contacting the solution with a lipase, wherein the lipase is *Alcaligenes* sp. lipase or *Psudomonas* sp lipase;
   wherein at least one of R₁ and R₂ is —H.

17. The method of claim 16 wherein $R_1$ and $R_2$ are both —H.

18. The method of claim 16 wherein the lipase is fixed.

19. The method of claim 16 wherein the lipase is free.

20. The method of claim 16 wherein the esterifying agent is selected from the group consisting of alkyl and vinyl esters of lower alkyl carboxylic acids having 2 to 6 carbon atoms.

21. The method of claim 20 wherein the esterifying agent is selected from the group consisting of ethyl acetate, vinyl acetate, and vinyl butyrate.

22. The method of claim 16 wherein the organic solvent is a linear or branched alkane having up to 12 carbon atoms, a dialkyl ether, or an alkyl ester of an alkyl carboxylic acid.

23. The method of claim 21 wherein the solvent is selected from the group consisting of hexane, ethyl acetate, carbon tetrachloride and diisopropyl ether.

24. The method of claim 22 wherein the solvent is selected from the group consisting of hexane, ethyl acetate, carbon tetrachloride and diisopropyl ether.

* * * * *